(12) United States Patent
Amador

(10) Patent No.: US 7,780,640 B1
(45) Date of Patent: Aug. 24, 2010

(54) SPILL PROOF CATHETER COLLECTOR BAG

(76) Inventor: Jesus O Amador, 2340 Naples Trace Cir., Unit 4, Naples, FL (US) 34109

( * ) Notice: Subject to any disclaimer, the term of this patent is extended or adjusted under 35 U.S.C. 154(b) by 470 days.

(21) Appl. No.: 11/627,895

(22) Filed: Jan. 26, 2007

(51) Int. Cl.
*A61M 1/00* (2006.01)

(52) U.S. Cl. .................................... 604/317

(58) Field of Classification Search .............. 604/317, 604/322

See application file for complete search history.

(56) References Cited

U.S. PATENT DOCUMENTS

| 3,092,279 | A | * | 6/1963 | Stevens | 215/246 |
| 3,186,409 | A | | 6/1965 | Bartz | |
| 3,415,299 | A | | 12/1968 | Hinman, Jr. et al. | |
| 3,529,599 | A | | 9/1970 | Folkman et al. | |
| 3,776,231 | A | | 12/1973 | Holbrook et al. | |
| 4,312,352 | A | * | 1/1982 | Meisch et al. | 604/322 |
| 4,743,236 | A | | 5/1988 | Manschot | |
| 4,913,161 | A | | 4/1990 | Villari et al. | |
| 6,652,495 | B1 | | 11/2003 | Walker | |
| 6,860,162 | B1 | * | 3/2005 | Jaeger | 73/863.85 |

FOREIGN PATENT DOCUMENTS

| CA | 2.036.950 | 8/1992 |
| WO | WO03/002043 | 1/2003 |

* cited by examiner

*Primary Examiner*—Tatyana Zalukaeva
*Assistant Examiner*—Benedict L Hanrahan
(74) *Attorney, Agent, or Firm*—Michael I. Kroll

(57) ABSTRACT

A collector bag for a catheter comprising a first receptacle and second receptacle selectively fastenable to each other. The first receptacle, serving as a temporary reservoir for fluids while the second receptacle is detached for disposal of its contents. The first has a top end with a throughbore forming a catheter attachment port while the bottom end incorporates a valve movable between an open and closed position thereby controlling the flow of fluids therebetween. The second receptacle serves as the primary receptacle for collecting fluids with a collar serving as receiver for the first receptacle bottom end that once inserted rotation of one member relative to the other in a predetermined direction locks the two receptacle together. Once fastened thereto, the valve can be opened to provide for fluid passage between the first and second receptacle. As needed, the valve can be closed and the second receptacle rotated to a point of detachment from the first whereby the first, with the valve closed serves as a temporary receptacle for fluids while the contents of the second are discarded.

20 Claims, 9 Drawing Sheets

SPILL PROOF CATHETER COLLECTOR BAG

BACKGROUND OF THE INVENTION

1. Field of the Invention

The present invention relates generally to collector receptacles and, more specifically, to a collector bag for a catheter comprising a first receptacle and second receptacle selectively fastenable to each other. The first receptacle, serving as a temporary reservoir for fluids while the second receptacle is detached for disposal of its contents. The first has a top end with a throughbore forming a catheter attachment port while the bottom end incorporates a valve movable between an open and closed position thereby controlling the flow of fluids therebetween. The second receptacle serves as the primary receptacle for collecting fluids with a collar serving as receiver for the first receptacle bottom end that once inserted rotation of one member relative to the other in a predetermined direction locks the two receptacles together. Once fastened thereto, the valve can be opened to provide for fluid passage between the first and second receptacle. As needed, the valve can be closed and the second receptacle rotated to a point of detachment from the first whereby the first, with the valve closed serves as a temporary receptacle for fluids while the contents of the second are discarded. Additionally the first receptacle may be utilized as a leg bag and as a means for eliminating the scent of urine in a room during disposal of collected urine.

2. Description of the Prior Art

There are other receptacle devices designed for collection. Typical of these is U.S. Pat. No. 3,186,409 issued to Bartz on Jun. 1, 1965.

Another patent was issued to Hinman, Jr. et al. on Dec. 10, 1968 as U.S. Pat. No. 3,415,299. Yet another U.S. Pat. No. 3,529,599 was issued to Folkman on Sep. 22, 1970 and still yet another was issued on Dec. 4, 1973 to Holbrook et al. as U.S. Pat. No. 3,776,231.

Another patent was issued to Meisch et al. on Jan. 26, 1982 as U.S. Pat. No. 4,312,352. Yet another U.S. Pat. No. 4,743,236 was issued to Manschot on May 10, 1988. Another was issued to Villari, et al. on Apr. 3, 1990 as U.S. Pat. No. 4,913,161 and still yet another was issued on Nov. 25, 2003 to Walker as U.S. Pat. No. 6,652,495.

Another patent was issued to Jurisich on Aug. 23, 1992 as Canada Patent No. CA2,036,950. Yet another International Patent Application No. WO03/002043 was published on Jan. 9, 2003 to Tanghoj.

U.S. Pat. No. 3,186,409

Inventor: Frank J. Bartz

Issued: Jun. 1, 1965

A drainage bag formed of superimposed sheets of flexible plastic material secured together about the edges, one of said sheets having an opening in the upper portion for receiving a drainage tube, a sealing tape disposed over the opening and secured to the surrounding portions of the sheet, said tape being adapted to be peeled away from the sheet to expose the opening, and to be readhered to the sheet to enable it to retain a drainage tube in position in the opening, said sheets also being secured together along a transverse support seal line spaced below the upper edge a distance which is a relatively small proportion of the total height of the bag, and adhesive attaching means disposed on one of the sheets, said adhesive attaching means being transversely disposed over and secured to the portion of the sheet which includes said transverse support seal line and also is disposed over and secured to the portion of the sheet disposed above said seal line, whereby when said adhesive attaching means is adhered to a support, downward forces applied to said sheets is transmitted through said transverse support seal line to the support and substantially no peeling force is applied to the adhesive attaching means at the uppermost portion thereof.

U.S. Pat. No. 3,415,299

Inventor: Frank Hinman, Jr., et al.

Issued: Dec. 10, 1968

A combination for handling urine comprising: a container with an inlet for connecting to a conduit leading from a patient and with an outlet at its bottom for draining urine from the container; an emptying tube with a longitudinal passage therethrough, said tube connected to the container's outlet and extending downwardly from the container's outlet to the tube's lower end; a rigid housing connected to the tube, which housing has a wall spacedly supported a distance from the tube's lower end, said housing having a mouth of greater cross-sectional area than the cross-sectional area of the tube's passage at its lower end; a removable closure closing of [ the housing's mouth; and a manually manipulable means for opening and closing the passage through said tube.

U.S. Pat. No. 3,529,599

Inventor: Bern D. Folkman

Issued: Sep. 22, 1970

For collecting urine from a patient a container with a drip housing fitting within its tubular neck. This drip housing has a one-way disk valve at its outlet and includes a double vent system to protect the patient. The drip housing provides an air break in the urine column from the patient and prevents urine from backing up into the patient's bladder from the container. When the container is full, it can be emptied through a sliding valve at its bottom while the container is still attached to a flexible collection tube leading from the patient.

U.S. Pat. No. 3,776,231

Inventor: Le Grand K. Holbrook

Issued: Dec. 4, 1973

A urinary drainage system and structure providing an initial or receiving container and also a sump or storage container. The two containers are interconnected, with the first being pivotal relative to the second so that the contents of the receiving container may be emptied into the storage container. Pivotal structure cooperating with the containers serves as journaling means and also inter-communication means to accommodate fluid flow, whether the receiving container is in its normal or tilted condition. Selfadjusting securement means is provided so the structure may be leveled regardless of the supporting structure. Independent drainage means for the containers are provided.

U.S. Pat. No. 4,312,352

Inventor: Meisch, et al.

Issued: Jan. 26, 1982

A unitary carrying handle-support hook assembly for urine drainage bags molded from a single plastic piece and including a pair of hanger hooks connected by a living hinge to a main frame which is provided with finger receiving apertures. The hooks can be stowed and latched in a nonuse position. The assembly includes opposed arm members receivable in pockets adjacent the top of the drainage bag.

U.S. Pat. No. 4,743,236

Inventor: James G. Manschot

Issued: May 10, 1988

A urine collection device having a meter and collection chamber formed by a heat sealed portion which separates the two chambers. A passageway formed by the heat sealed portion and a sealed edge allows the collected urine to pass from one chamber to the other and dispensed from a discharge port when the urine collection device is hung selectively from either of two hangers located on the edges of the device.

U.S. Pat. No. 4,913,161

Inventor: Frank Villari, et al.

Issued: Apr. 3, 1990

The present invention comprises a urine collection bag with a tilt bag indicator on the front wall thereof. The indicator comprises a clear patch or housing disposed to the side of the input conduit of the containment bag. An orifice is disposed through the front wall to provide communication between the chamber of the collection bag and the chamber defined by the transparent patch and the front wall of the bag. If the bag is tilted, urine will escape the collection bag chamber and go into the indicator chamber, and be trapped there. This will alert appropriate medical personnel that a reflux of urine up the input conduit, thus allowing whatever corrective action be taken, as necessary.

U.S. Pat. No. 6,652,495

Inventor: Kenneth Gordon Walker

Issued: Nov. 25, 2003

A system for disposing of body fluids collected during surgery comprises a canister and an apparatus for emptying and cleaning the canister. The canister has a lid having an inlet port to receive body fluids during surgery and for insertion of a cleaning fluid sprayer during servicing, an outlet port with a suction tube extending into the canister for removal of fluids therefrom, and a vacuum port for the application of vacuum to the canister. The servicing unit is an appliance having a receiving compartment in which the canister is placed. A connector head in the servicing unit connects the canister to a source of cleaning fluid and to a conduit for evacuating the fluids in the canister through the suction tube and to a decontamination chamber, where they are brought into contact with a disinfecting fluid, and subsequently to a drain.

Canadian Patent Number CA2,036,950

Inventor: Dragoslav Jurisich

Issued: Aug. 23, 1992

My invention is an improvement of all open end ostomy appliances used to collect feces or urine from bodies which eliminate food and water residues through a surgically created opening generally called stoma. My ostomy bag will not be open at the end, as all ostomy appliances are. Instead it will be open on the upper left or right side of it. This improvement will eliminate one problem and greatly reduce another one. (a) It will eliminate the rubbing caused by the tail end closure—a variety of clasps usually made of plastic materials—which pinch, prick, and hurt the crotch and the tender parts of the body near it. (b) It will greatly reduce the risk of spillage, which occurs too frequently due to the pressure of the collected secretion on a clasp—any clasp used for closing an ostomy appliance. When this happens, the contents of the bag are released into the user's underwear and down his or her legs, causing some very embarrassing and uncomfortable situations. Those clasps also open frequently, even if the amount of the collected refuse in the appliance is rather small. It may open when ostomates work in a crouching position, or during physical exercises, because a moveable part of the body—that is the upper parts of a leg—will often cause the clasp lose its grip. Also a clasp may weaken before one would expect that to happen. But if the opening of an appliance is in its upper part the spillage will be much lesser even if the clasp ceases to work. Moreover, the clasp will be located above the crotch, near a part of the body which is less active, and therefore less prone to cause the opening of the clasp. But, more importantly, the pressure of the collected feces and urine on the clasp will be considerably smaller in those upper location.

International Patent Application Number WO03/002043

Inventor: Allan Tanghoj

Issued: Jan. 9, 2003

The present invention as a bag for collecting boldily fluids such as urine. The bag is adapted for use e.g. in connection with a catheter and is provided with supporting means allowing handling of a liquid-filled bag without squeezing the bag and thus without the risk of contaminating the surroundings. The bag is provided with a draining spout allowing the liquid-filled bag to be emptied without spillage.

While these collector devices may be suitable for the purposes for which they were designed, they would not be as suitable for the purposes of the present invention, as hereinafter described.

SUMMARY OF THE PRESENT INVENTION

A primary object of the present invention is to provide an improved drainage receptacle for a catheter.

Another object of the present invention is to provide a drainage receptacle comprised of a pair of receptacles.

Yet another object of the present invention is to provide a drainage receptacle wherein said receptacles are in communication with each other having flow control means positioned therebetween.

Still yet another object of the present invention is to provide a drainage receptacle wherein said receptacles are selectively separable from each other.

Additional objects of the present invention will appear as the description proceeds.

The present invention overcomes the shortcomings of the prior art by providing a collector bag for a catheter comprising a first receptacle and second receptacle selectively fastenable to each other. The first receptacle, serving as a temporary reservoir for fluids while the second receptacle is detached for disposal of its contents. The first has a top end with a throughbore forming a catheter attachment port while the bottom end incorporates a valve movable between an open and closed position thereby controlling the flow of fluids therebetween. The second receptacle serves as the primary receptacle for collecting fluids with a collar serving as receiver for the first receptacle bottom end that once inserted rotation of one member relative to the other in a predetermined direction locks the two receptacle together. Once fastened thereto, the valve can be opened to provide for fluid passage between the first and second receptacle. As needed, the valve can be closed and the second receptacle rotated to a point of detachment from the first whereby the first, with the valve closed serves as a temporary receptacle for fluids while the contents of the second are discarded. Additionally the first receptacle may be utilized as a leg bag and as a means for eliminating the scent of urine in a room during disposal of collected urine.

The foregoing and other objects and advantages will appear from the description to follow. In the description reference is made to the accompanying drawings, which forms a part hereof, and in which is shown by way of illustration specific embodiments in which the invention may be practiced. These embodiments will be described in sufficient detail to enable those skilled in the art to practice the invention, and it is to be understood that other embodiments may be utilized and that structural changes may be made without departing from the scope of the invention. In the accompanying drawings, like reference characters designate the same or similar parts throughout the several views.

The following detailed description is, therefore, not to be taken in a limiting sense, and the scope of the present invention is best defined by the appended claims.

BRIEF DESCRIPTION OF THE DRAWING FIGURES

In order that the invention may be more fully understood, it will now be described, by way of example, with reference to the accompanying drawing in which.

DESCRIPTION OF THE REFERENCED NUMERALS

Figure 1:
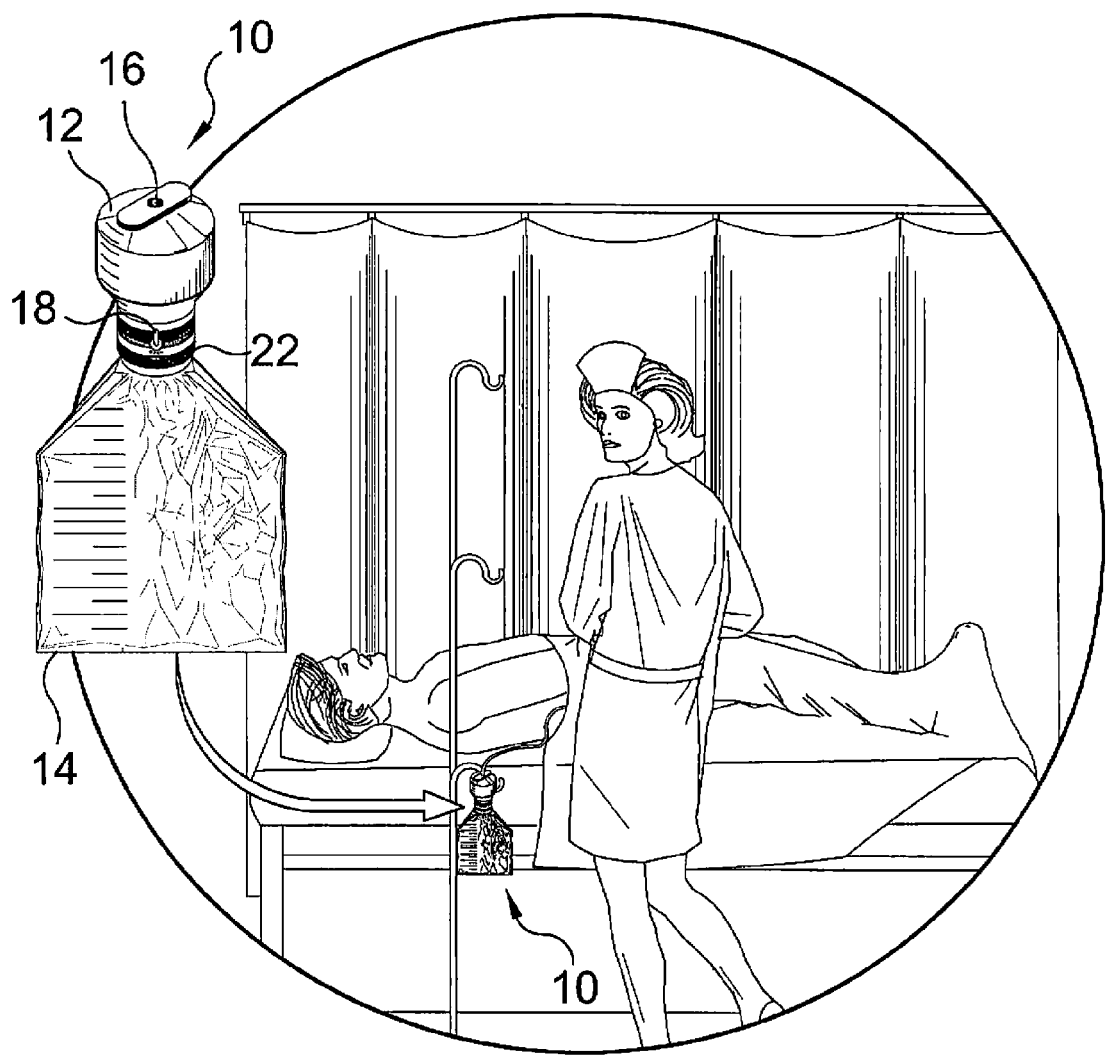
FIG. 1 is an illustrative view of the present invention in use.

Turning now descriptively to the drawings, in which similar reference characters denote similar elements throughout the several views, the figures illustrate the spill proof catheter collection bag of the present invention. With regard to the reference numerals used, the following numbering is used throughout the various drawing figures.

10 present invention
12 first receptacle
14 second receptacle
16 catheter attachment port
18 valve
19 throughbore
20 twist lock coupling means
22 twist lock collar
24 catheter tube
26 back support
28 urine
30 handle
32 locking element
34 locking flange
36 notches
38 nibs
40 gasket
42 inner walls
44 securing device
46 reduction lip
48 open slot
50 hook and loop straps

DETAILED DESCRIPTION OF THE PREFERRED EMBODIMENT

The following discussion describes in detail one embodiment of the invention (and several variations of that embodiment). This discussion should not be construed, however, as limiting the invention to those particular embodiments, practitioners skilled in the art will recognize numerous other embodiments as well. For definition of the complete scope of the invention, the reader is directed to appended claims.

FIG. 1 is an illustrative view of the present invention 10 in use. The present invention is a collection device or improved catheter drainage bag 10 comprising a first receptacle 12 and second receptacle 14 selectively fastenable to each other. The first receptacle 12 serves as a temporary reservoir for fluids while the second receptacle 14 is detached for disposal of its contents. The first receptacle 12 has a top end with a throughbore forming a catheter attachment port 16 while the bottom end incorporates a valve 18 movable between an open and closed position thereby controlling the flow of fluids therebetween. The second receptacle 14 serves as the primary drainage bag for collecting fluids with a twist-lock collar 22 serving as receiver for the first receptacle 12 bottom end that, once inserted, rotation of one member relative to the other in a predetermined direction locks the two receptacles together. Once fastened thereto, the valve 18 can be opened to provide for fluid passage between the first 12 and second receptacle 14.

Figure 2:
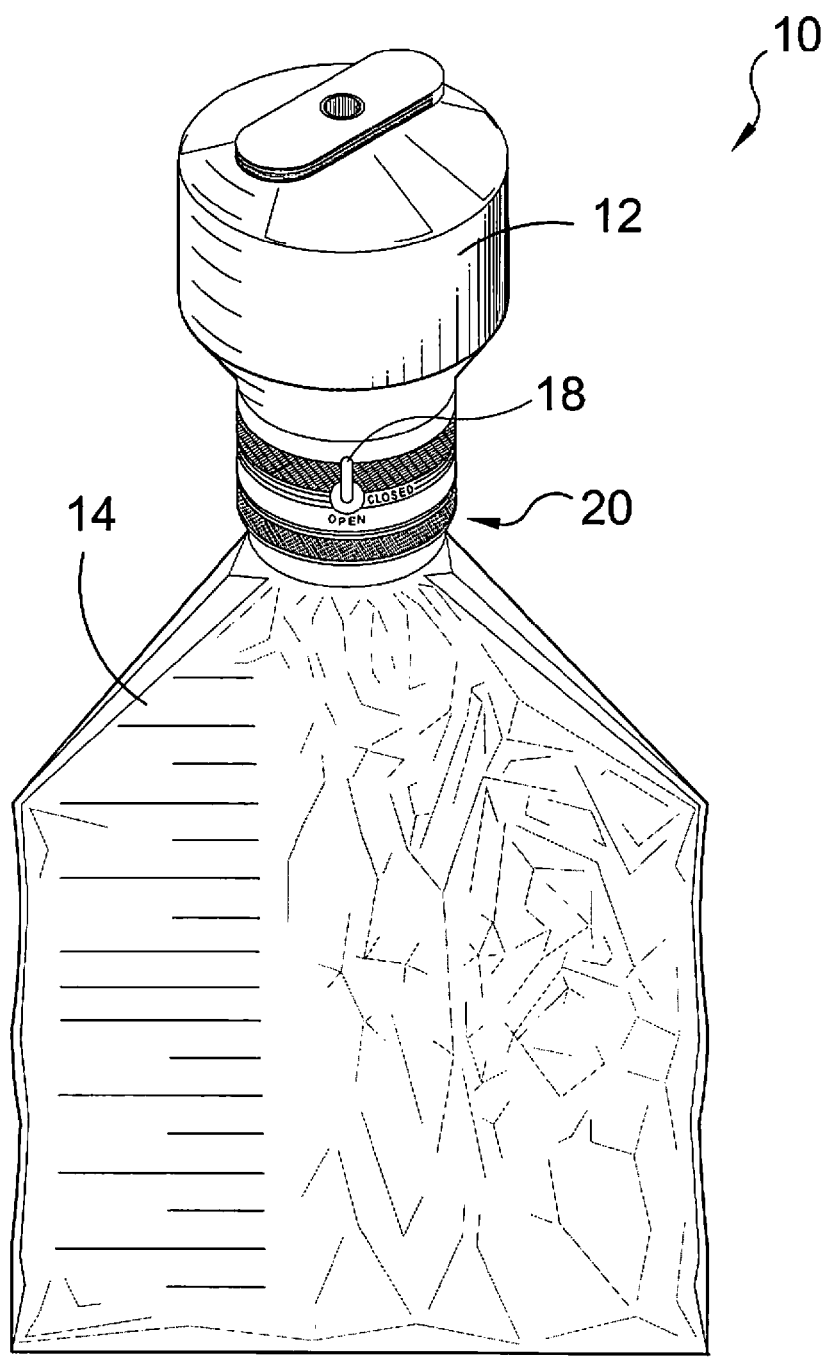
FIG. 2 is a perspective view of the present invention.

FIG. 2 is a perspective view of the present invention 10. Shown is a perspective view of the spill proof bedside catheter drainage bag 10 having a first receptacle 12 and a second receptacle 14 with flow control means 18 disposed between them and twist lock coupling means 20 whereby each is separable from the other. The flow control means is a ball valve 18 for preventing flow from the first receptacle 12 to the second 14 with each having mating twist lock 20 components. The design in shape will allow disposing of urine without the use of other utilities and facilitates a nurse's ability to take urine samples. The second receptacle 14 is easily removable from the first receptacle 12 without disturbing the patient using said device. Additionally the first receptacle 12 may be utilized as a leg bag and as a means for eliminating the scent of urine in a room during disposal of collected urine.

Figure 3:
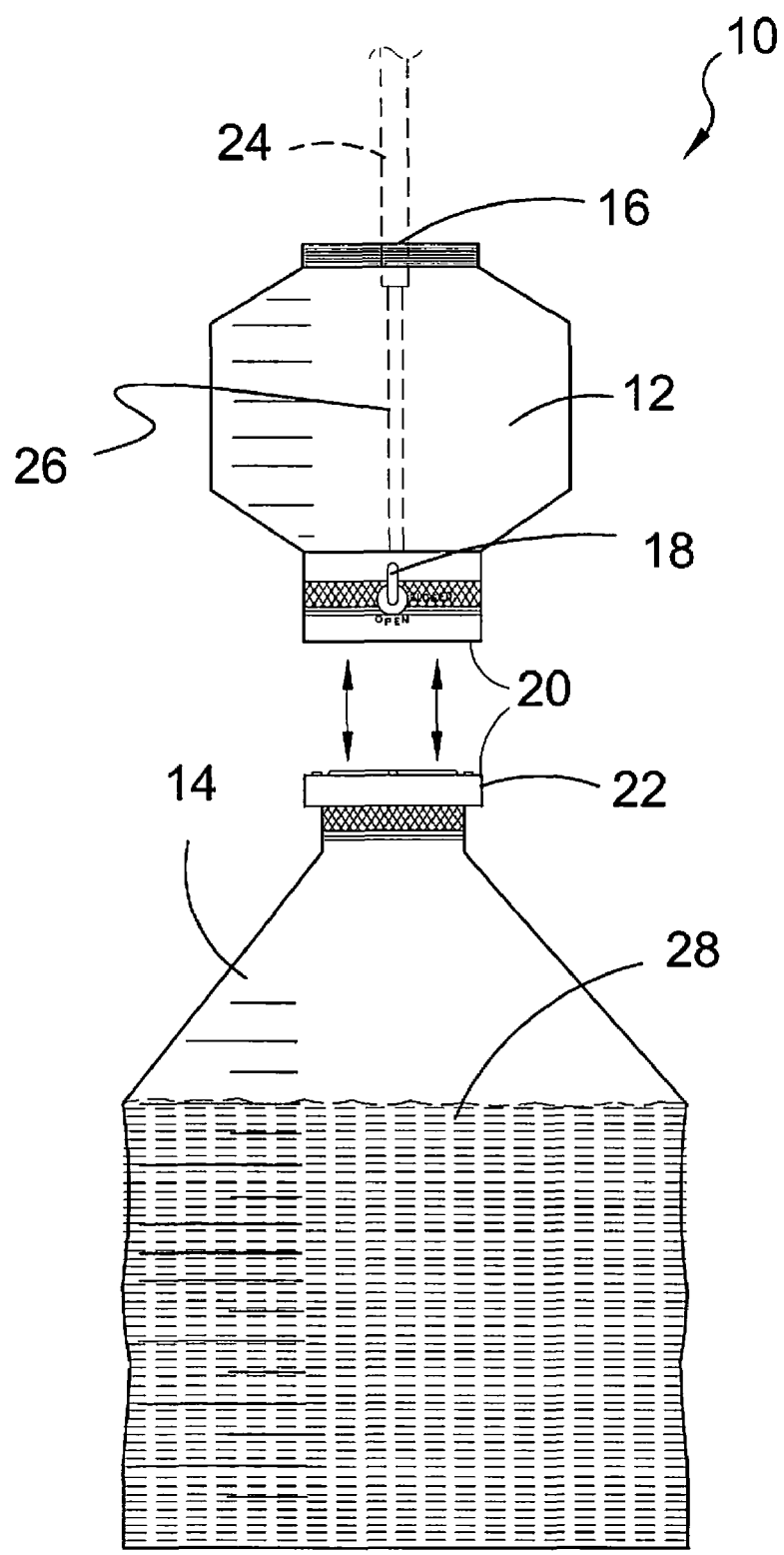
FIG. 3 is a frontal view of the present invention.

FIG. 3 is a frontal view of the present invention 10 comprising first 12 and second 14 separable receptacles in a detached state with the first receptacle 12 incorporating means for preventing flow to the second receptacle 14 through employment of a shutoff valve 18 thereby providing means for removing the second receptacle 14 without compromising the collection ability of the apparatus since the first receptacle 12 serves as temporary reservoir until a second receptacle 14 is connected thereto and the first receptacle 12 valve 18 opened. Shown is the catheter tube 24 inserted through the catheter port 16 and in communication with a plastic back support 26. Additionally, the first receptacle 12 may be utilized as a leg bag and as a means for eliminating the scent of urine in a room during disposal of collected urine 28. The first receptacle 12 is detached from the second receptacle 14 through the use of mating twist-lock coupling means 20 including a twist lock collar 22.

Figure 4:
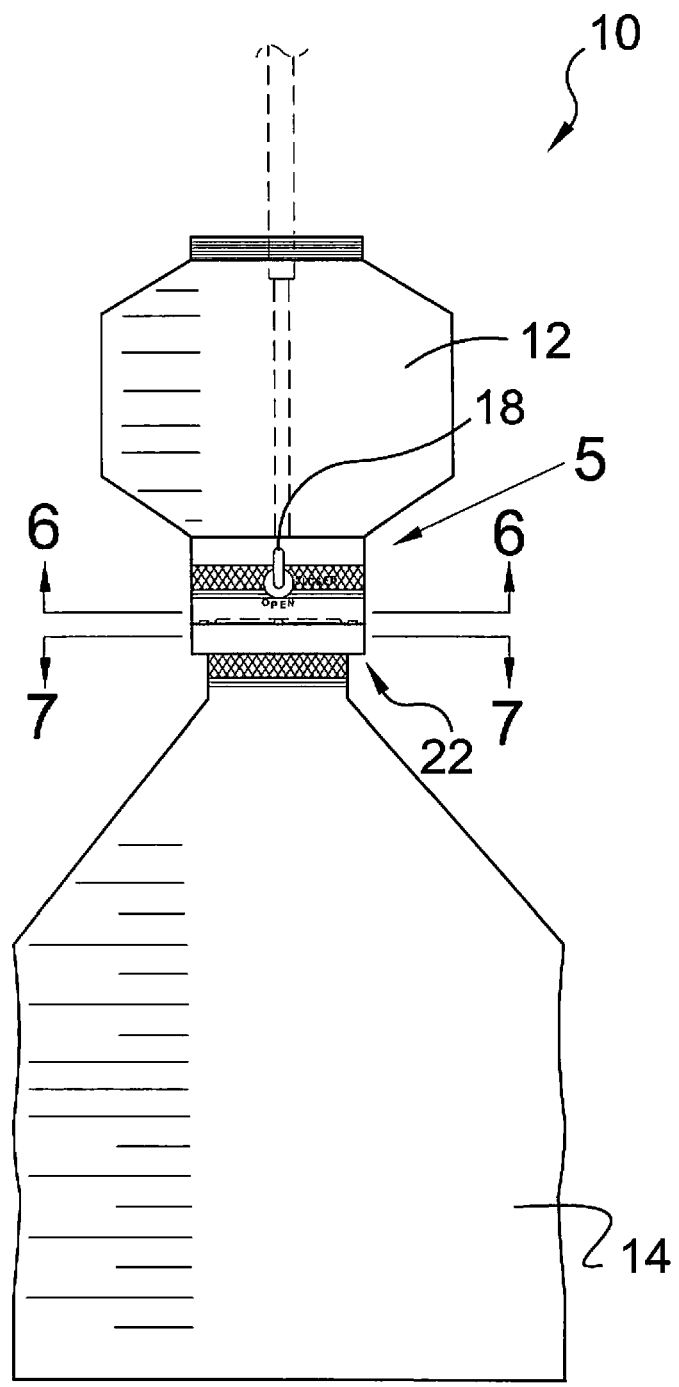
FIG. 4 is a frontal view of the present invention.

FIG. 4 is a frontal view of the present invention 10. Shown is a frontal view of the present invention 10 comprising first 12 and second 14 separable receptacles in an attached state through engagement of a twist lock coupling means 20 forming an integral part of each receptacle. Once engaged, flow between the receptacles is controlled through the open or closed state of the shutoff valve 18 forming an integral part of the first receptacle 12. Additionally the first receptacle 12 may be utilized as a leg bag and as a means for eliminating the scent of urine in a room during disposal of collected urine.

Figure 5:
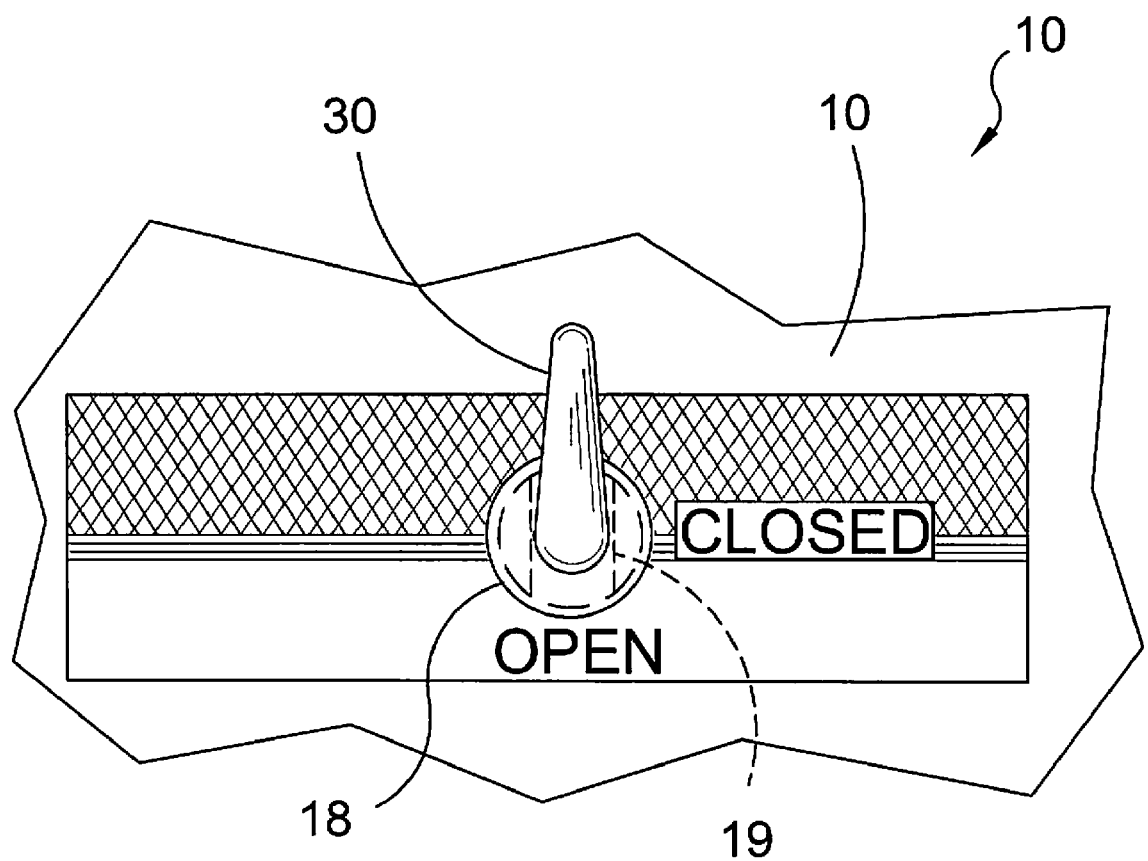
FIG. 5 is an enlarged view of the shutoff valve.

FIG. 5 is an enlarged view of the shutoff valve 18 that forms an integral part of the first receptacle 12. The valve 18 serves to prevent flow between the first 12 and second receptacle. While various valves would serve to cutoff flow, preferably a simple ball valve would suffice with the exterior handle 30 co-parallel with said throughbore 19 and positioned in such a way that vertically flow is provided for while horizontally flow is impeded.

Figure 6:
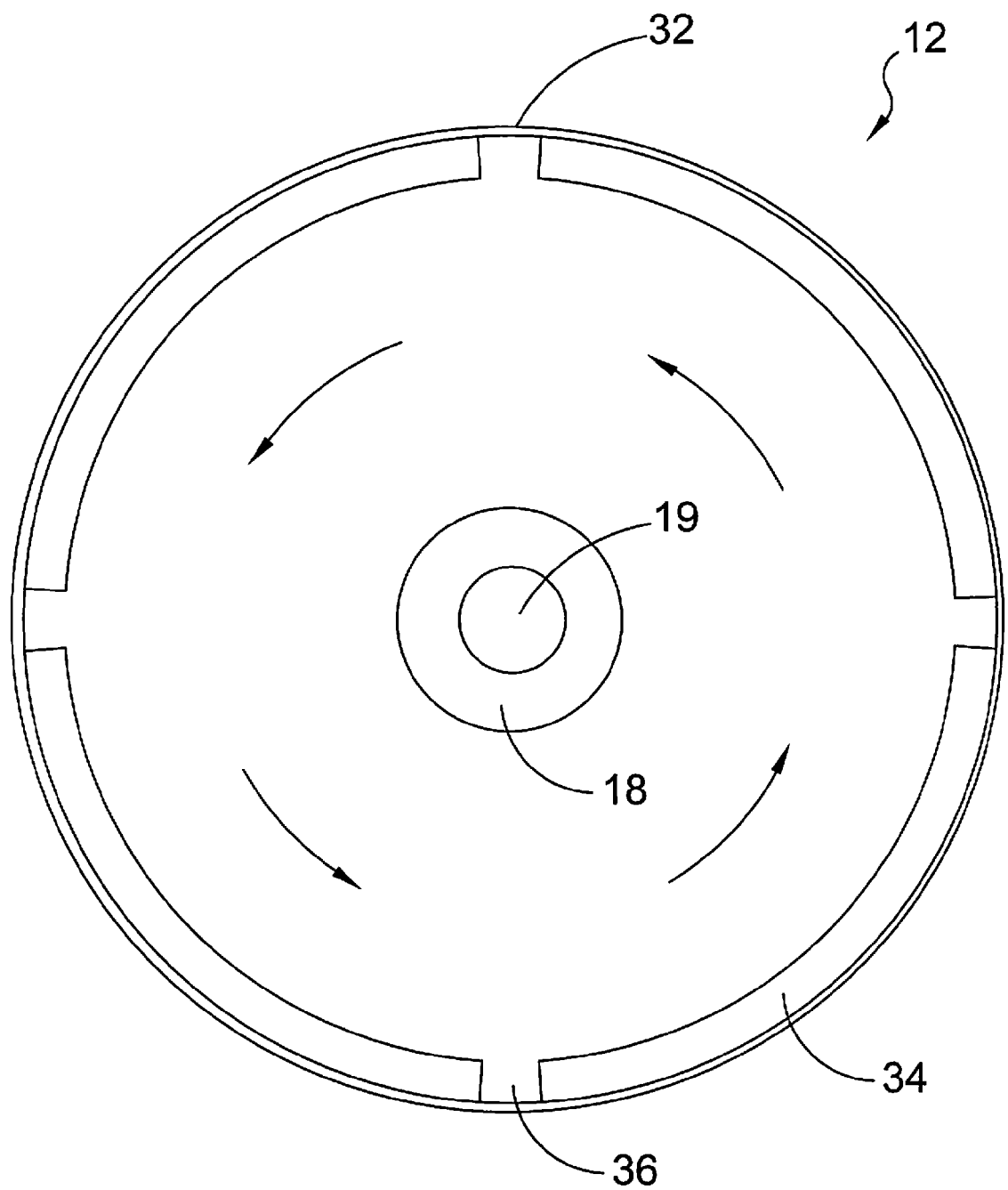
FIG. 6 is a cross sectional view of the upper portion of the locking element of the present invention.

FIG. 6 is a cross sectional view of the locking element 32 disposed on the bottom of the first receptacle 12. Shown is a locking flange 34 interiorly disposed along the circumference of the locking element 32 of the first receptacle 12. The twist-lock collar has locking nibs depending therefrom while the locking flange 34 has reciprocal notches 36 conformed to align with the nibs and communicates with channels whereby one is rotative relative to the other.

Figure 7:
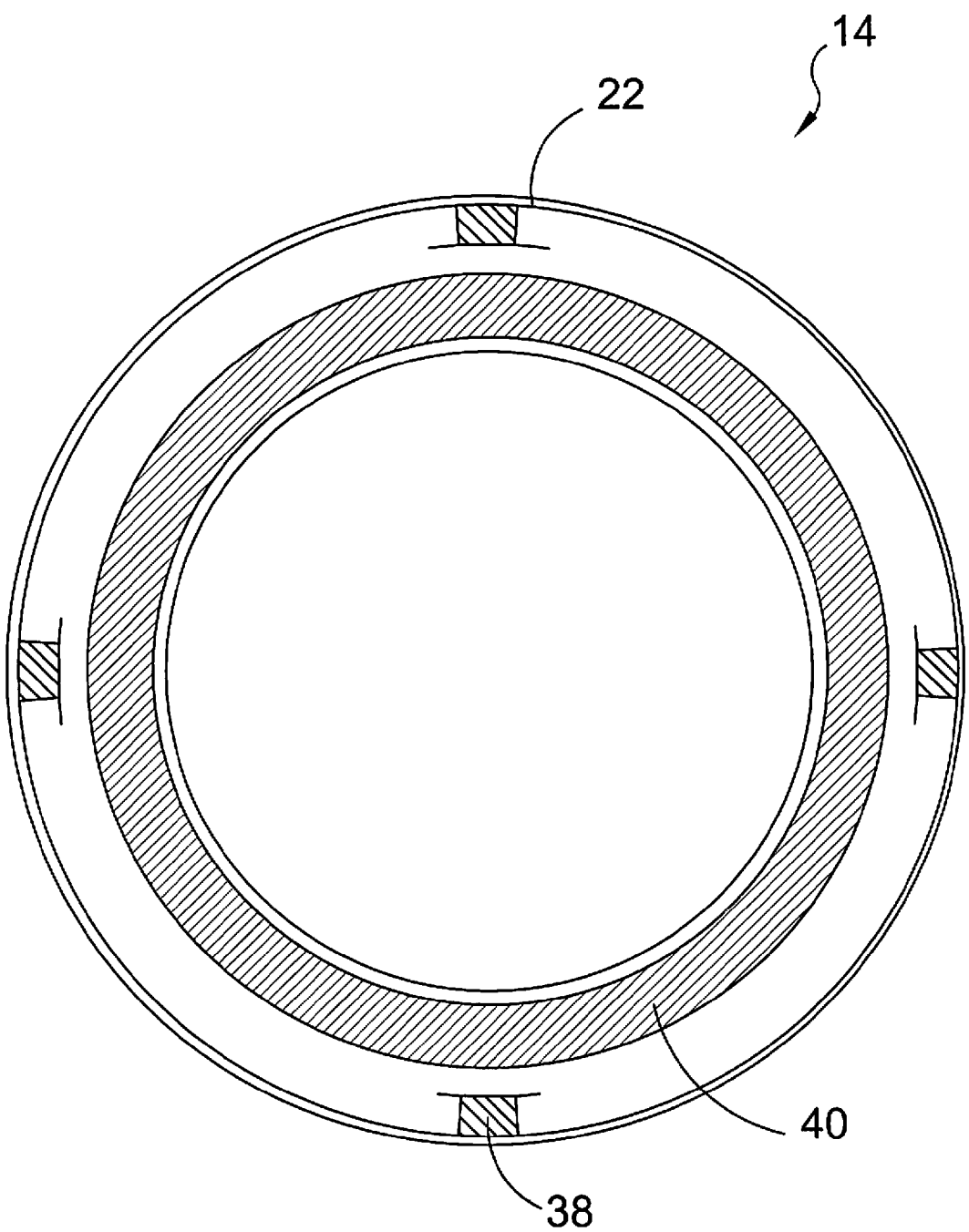
FIG. 7 is a cross sectional view of the lower portion of the locking element of the present invention.

FIG. 7 is a cross sectional view of the twist-lock collar 22 disposed on the top portion of the second receptacle 14. Shown is a top view of the locking collar 22 having a plurality of nibs 38 that are conformed to align with the notches on the locking flange of the locking element of the first receptacle. The nibs 38 are inserted therein and the collar 22 is rotated to secure the nibs 38 behind the locking flange and releasably engage the first receptacle with the second 14. To prevent seepage around the mating members, a compressable gasket 40 is provided.

Figure 8:
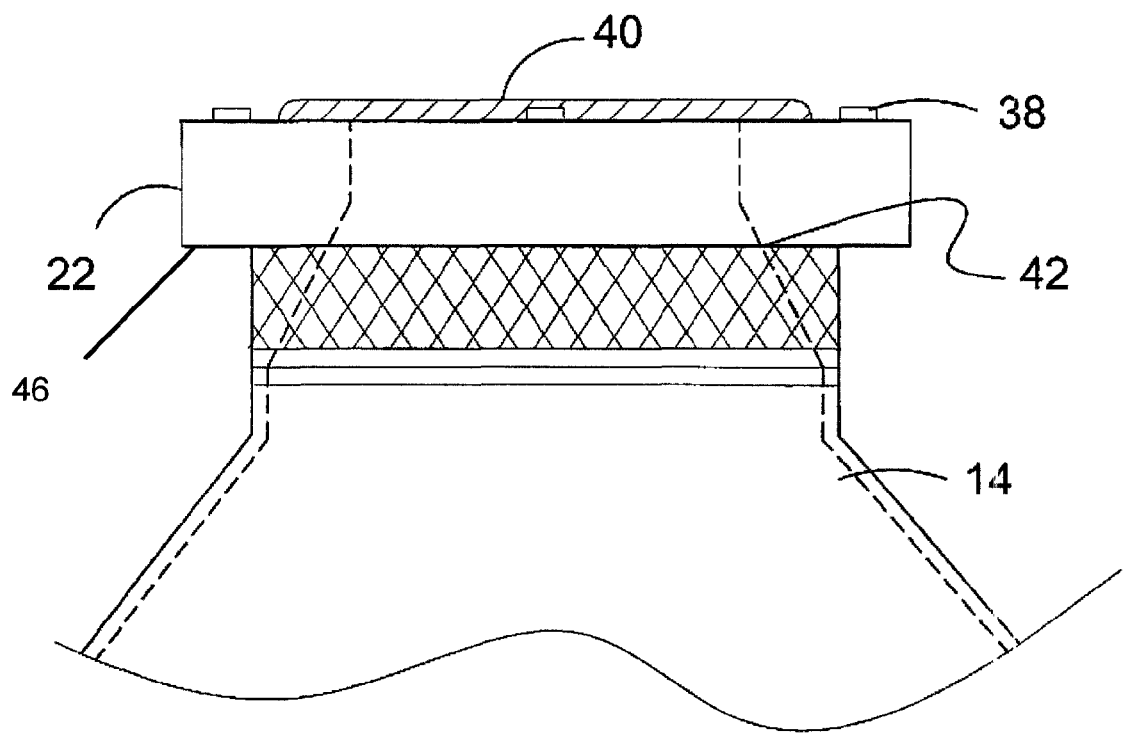
FIG. 8 is a detail view of the present invention.

FIG. 8 is a detail view of the twist-lock collar 22 of the second receptacle 14. Shown is a frontal view of the twist-lock collar 20 and the locking nibs 38 for engaging the twist-locking element of the first receptacle. To prevent seepage around the mating members, a compressable gasket 40 is provided. In addition, three main components of the second receptacle 14 comprising the compressible gasket 40, the twist-lock collar 22 and the sloping inner walls 42 of the lower bag provide means to ensure spill proof collection and ease the fluid from the first receptacle to the second receptacle 14. The twist-lock collar 22 is provided with a reduction lip 46.

Figure 9:
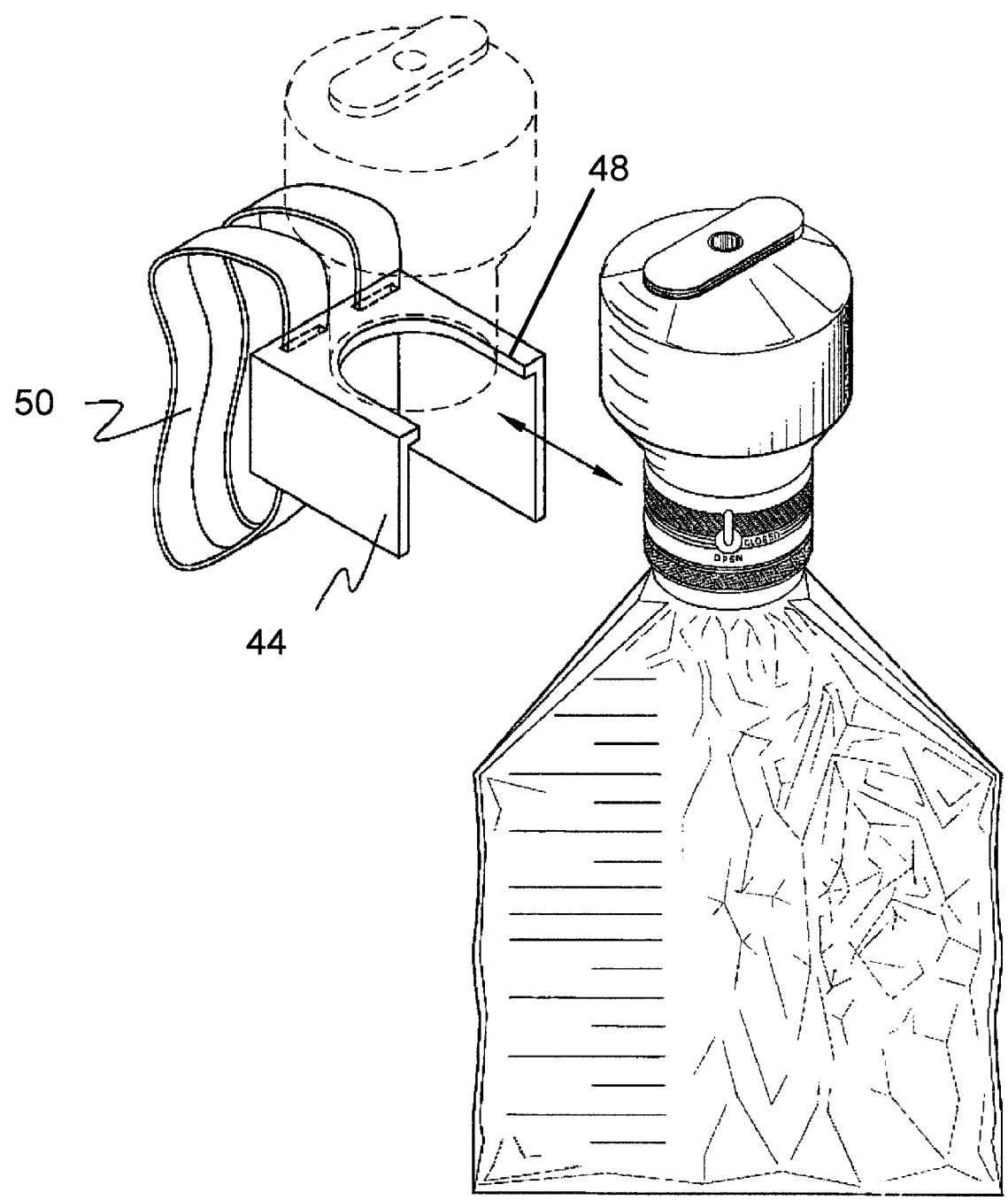
FIG. 9 is a perspective view of the present invention's securing device.

FIG. 9 is a perspective view of the present invention's 10 securing device 44. Depicted in this figure is a perspective view spill proof bedside drainage bag system 10 and securing device 44. A reduction lip in the twist-lock collar 22 and an open slot 48 in the securing device 44 provide means to secure the bedside collection device therein while allowing easy removal by pushing up and sliding the bag away from the open slot surface. Hook and loop straps 50 provide means to secure the securing device 44 to the bed frame or other structure.

It will be understood that each of the elements described above, or two or more together may also find a useful application in other types of methods differing from the type described above.

While certain novel features of this invention have been shown and described and are pointed out in the annexed claims, it is not intended to be limited to the details above, since it will be understood that various omissions, modifications, substitutions and changes in the forms and details of the device illustrated and in its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention

The invention claimed is:

1. An improved catheter bedside drainage bag system comprising:
   a) a first receptacle having a catheter attachment port disposed on the top portion thereof for receiving a catheter tube;
   b) a second receptacle;
   c) a twist lock coupling means for selectively attaching and detaching said second receptacle to said first receptacle; and
   d) a ball valve with a central throughbore for selectively allowing passage of fluid from said first receptacle to said second receptacle, said valve having an externally disposed handle for allowing the user to selectively permit and restrict fluid flow between said first receptacle and said second receptacle.

2. The improved catheter bedside drainage bag system recited in claim 1, wherein said twist-lock coupling means comprises a locking element disposed on the bottom portion of said first receptacle and a mating locking collar disposed on the top portion of said second receptacle.

3. The improved catheter bedside drainage bag system recited in claim 2, wherein said locking element has a peripheral flange extending medially therefrom with a plurality of notches disposed therein.

4. The improved catheter bedside drainage bag system recited in claim 3, wherein said locking collar includes a plurality of locking nibs extending therefrom corresponding with said notches in said flange and sized to facilitate the insertion of said nibs therein when aligned therewith.

5. The improved catheter bedside drainage bag system recited in claim 4, wherein said twist-lock collar is partially rotated once said nibs are inserted into said notches thereby creating the misalignment thereof and effectively securing said second receptacle to said first receptacle.

6. The improved catheter bedside drainage bag system recited in claim 1, wherein said valve member is disposed on the bottom portion of said first receptacle proximal to said locking element.

7. The improved catheter bedside drainage bag system recited in claim 1, wherein said handle is co-parallel with said throughbore and when positioned in a vertical orientation permits the flow of fluid therethrough from said first receptacle to said second receptacle and when positioned in a substantially horizontal orientation restricts the flow therethrough.

8. The improved catheter bedside drainage bag system recited in claim 7, wherein said twist-lock collar further includes a leak proof seal to prevent fluid from escaping through said coupling while fluid is passing therethrough.

9. The improved catheter bedside drainage bag system recited in claim 8, wherein said leak proof seal is a compression gasket.

10. The improved catheter bedside drainage bag system recited in claim 9, wherein one end of said catheter is connected to the patient and the other is inserted into said catheter attachment port in said first receptacle.

11. The improved catheter bedside drainage bag system recited in claim 10, wherein said second receptacle is connected to said first receptacle utilizing said twist-lock coupling means.

12. The improved catheter bedside drainage bag system recited in claim 11, wherein said ball valve is disposed in the open position thus facilitating the flow of fluid from said first receptacle into said second receptacle.

13. The improved catheter bedside drainage bag system recited in claim 12, wherein said valve remains open until said second receptacle is substantially full whereupon said valve is closed and said second receptacle is removed for emptying and replacement while any subsequent fluid introduced to said first receptacle during that time is retained within said first receptacle due to the closed ball valve.

14. The improved catheter bedside drainage bag system recited in claim 13, wherein an empty second receptacle is secured to said first receptacle via said twist-lock coupling means and said ball valve is turned to the open position thereby allowing any fluid retained within said first receptacle to pass therethrough as well as any fluid subsequently introduced therein.

15. The improved catheter bedside drainage bag system recited in claim 1, further including a securing device to releasably fasten said catheter drainage bag to a bed frame or similar structure.

16. The improved catheter bedside drainage bag system recited in claim 15, wherein said twist-lock coupling means includes a reduction lip disposed towards the underside of said first receptacle.

17. The improved catheter bedside drainage bag system recited in claim 16, wherein said securing device includes an open slot for receiving said reduction lip therein.

18. The improved catheter bedside drainage bag system recited in claim 17, wherein said securing device further includes at least one strap for securement to a structure.

19. The improved catheter bedside drainage bag system recited in claim 18, wherein said catheter drainage bag is removed by said securing device by pushing up and sliding the bag away from said open slot.

20. The improved catheter bedside drainage bag system recited in claim 1, wherein said first receptacle further includes a plastic back support centrally disposed therein.

\* \* \* \* \*